(12) United States Patent
Malkki

(10) Patent No.: US 9,940,435 B2
(45) Date of Patent: Apr. 10, 2018

(54) VISUALIZATION OF A DEVELOPMENT AND ESCALATION OF A PATIENT MONITOR ALARM

(71) Applicant: General Electric Company, Schenectady, NY (US)

(72) Inventor: Esa Pekka Juhani Malkki, Järvenpää (FI)

(73) Assignee: GENERAL ELECTRIC COMPANY, Schenectady, NY (US)

(*) Notice: Subject to any disclaimer, the term of this patent is extended or adjusted under 35 U.S.C. 154(b) by 169 days.

(21) Appl. No.: 14/570,474

(22) Filed: Dec. 15, 2014

(65) Prior Publication Data

US 2016/0166148 A1   Jun. 16, 2016

(51) Int. Cl.
| | |
|---|---|
| *G08C 19/22* | (2006.01) |
| *H04Q 9/00* | (2006.01) |
| *G06F 19/00* | (2018.01) |
| *A61B 5/00* | (2006.01) |
| *A61B 5/0205* | (2006.01) |

(52) U.S. Cl.
CPC ........ *G06F 19/3406* (2013.01); *A61B 5/0205* (2013.01); *A61B 5/742* (2013.01); *A61B 5/746* (2013.01)

(58) Field of Classification Search
CPC .................................................. G06F 19/3406
USPC ...................................... 340/870.07
See application file for complete search history.

(56) References Cited

U.S. PATENT DOCUMENTS

| | | | | |
|---|---|---|---|---|
| 2004/0054261 A1* | 3/2004 | Kamataki | ............ | A61B 5/0002 600/300 |
| 2011/0118573 A1* | 5/2011 | McKenna | ............ | A61B 5/0205 600/323 |
| 2013/0246089 A1* | 9/2013 | Gross | .................. | G06F 19/3406 705/2 |
| 2014/0266709 A1* | 9/2014 | Nagase | ................ | G08B 25/001 340/539.13 |
| 2015/0094546 A1* | 4/2015 | Al-Ali | .................. | A61B 5/0205 600/301 |
| 2015/0350749 A1* | 12/2015 | Pybus | ...................... | H04Q 9/00 340/870.09 |
| 2015/0371418 A1* | 12/2015 | Laycock | ............... | G06T 11/206 345/440 |

* cited by examiner

*Primary Examiner* — Fabricio R Murillo Garcia

(57) ABSTRACT

In the present invention, a monitoring device for providing information on data obtained from sensors operably connected to the device includes a central processing unit configured to receive incoming data signals from a sensor concerning a physiological parameter and to compare the incoming data signals to predetermined alarm criteria for the physiological parameter to determine an alarm condition. The device also includes a display operably connected to the central processing unit and having a display screen with a display area configured to visually represent the incoming data signals concerning the physiological parameter relating to a determined alarm condition on a portion of the display area in a visually distinct manner from a remainder of the display area to visually illustrate an escalation effect.

18 Claims, 5 Drawing Sheets

VISUALIZATION OF A DEVELOPMENT AND ESCALATION OF A PATIENT MONITOR ALARM

BACKGROUND OF THE INVENTION

The invention relates generally to monitors or displays connected to monitoring or diagnostic equipment for illustrating data about an object to which the equipment is connected, and more particularly to devices and methods for graphically displaying the data.

In monitoring or diagnostic devices that are currently utilized, the data obtained by the devices is often shown on a display connected to the device that provides a visual representation of the data in manner that can be readily assimilated by an individual viewing the data.

These types of devices are utilized in many different environments, such as in hospitals and other medical environments where patients are continuously monitored by these devices. In the example of those devices utilized in medical environments, the data obtained and displayed on the monitoring or diagnostic devices is often shown as numerical values for the various parameters being monitored that are represented on a screen of the device. The clinicians observing the screen and the numerical values represented thereon derive the necessary information by viewing and analyzing the numerical values.

In collecting and formatting the data from the patient for display on the associated screen, the monitoring device can also generate alarms based on sensed events determined by the stored criteria and parameter limits regarding the data collected by the monitoring device and represented by the numerical values. In most situations, the alarms corresponding to the sensed events represented in the data in the displayed are various types of audio and or visual indicators generated from the monitoring device.

The visual alarm indicators normally consist of a flashing alarm icon on the screen of the device in or associated with bright, easily noticeable colors to indicate which parameter has to be reviewed by the individual on an urgent basis. Most often these visual indicators of alarms are limited to highlighting the numerical values which are abnormal optionally along with a display of the name of any critical cardiac event, e.g. ASYSTOLE.

However, in order for the alarm to be generated to display the associated numerical value in the highlighted format, the sensed values for the parameter must meet the criteria stored in the device for the alarm condition, such as exceeding a threshold value retained in the device. While the alarm condition can be determined by the device using one or more criteria to define the alarm condition, in prior art monitoring devices the alarm condition is either met or not met based on the data received by the device and compared with the corresponding alarm condition criteria. As a result, the alarm condition criteria are normally set at a relatively low level in order to trigger the alarm and draw the attention of the clinician to that parameter prior to the clinical alarm event reaching a critical stage. In certain prior art displays, ancillary display icons, such as arrows, are utilized with the displayed parameter values to provide an indication of the direction in which the particular parameter is trending. However, these additional icons require valuable space on the display screen and require that the individual look at a separate icon from the parameter display in order to view the information provided by the ancillary icon.

Further, while these devices provide displays and methods of operating the displays that are capable of organizing information relating to various alarm events or conditions for review by an individual, there are a large number of parameters presented on the screen at any given time. Due to the large number of the alarm events which may be occurring at a given time, partially as a result of the low threshold criteria values for triggering the alarms, certain highly important clinical events could inadvertently be overlooked or missed. This is often referred to, as alarm fatigue and results from the constant representation of the alarm events in a similar manner that can cause certain events to become "lost" in the flood of alarms and associated information represented on the display screen of the particular device.

Therefore, it is desirable to provide an improved system and method of identifying or highlighting alarm conditions that reduces the prevalence of alarm fatigue while concurrently increasing the effectiveness and amount of information provided by the alarm signaled by the device. In addition, it is desirable to provide the increased amount of information without increasing the number of display icons presented on the display screen.

BRIEF DESCRIPTION OF THE INVENTION

In the present invention, a monitoring or diagnostic device includes a display screen on which data concerning item being monitored by the device is represented. The incoming data signals received by the device are represented on the display screen as icons showing the sensed physiological parameter values represented by the incoming data signals to enable an individual viewing the display screen to determine the current operating condition or parameters of the item, such as a patient. The device and display screen can also illustrate various alarm conditions or events, as determined by the device from the incoming data signals received by the device from sensors attached to the patient being monitored. The alarm conditions or events are triggered by the comparison or application of preset criteria for the parameter(s) being sensed stored within the device to the incoming data signals from the sensors. The criteria can be selected as desired and often include a number of values or ranges of values corresponding to the particular parameter being monitored, such as predetermined maximum and minimum values or minimum and maximum frequencies for the incoming data signals, among others. The stored value ranges may also include a number of intermediate values corresponding to various levels of the progression or development of the associated alarm condition between the lowest and highest values of the ranges. Using these criteria, an alarm event or condition is initially determined by the device when the incoming data signal is compared and to the relevant alarm criteria. If the device determines that one or more of the alarm criteria are met, the device modifies the operation of the display feature concerning the sensed data by highlighting a portion of the display area including the display feature. As additional criteria for the sensed parameter are met by the incoming data signals, additional portions of the display area are highlighted, correspondingly illustrating the level of severity of the alarm event determined by the device. In this manner, the display effectively indicates to the observing clinician the severity or level of the alarm condition by the degree of highlighting of the relevant display feature or area, while also illustrating the value for the sensed parameter within the same display area.

It is to be understood that both the foregoing general description and the following detailed description are exemplary and explanatory and are intended to provide further explanation of the invention as claimed.

DETAILED DESCRIPTION OF THE INVENTION

Figure 1:
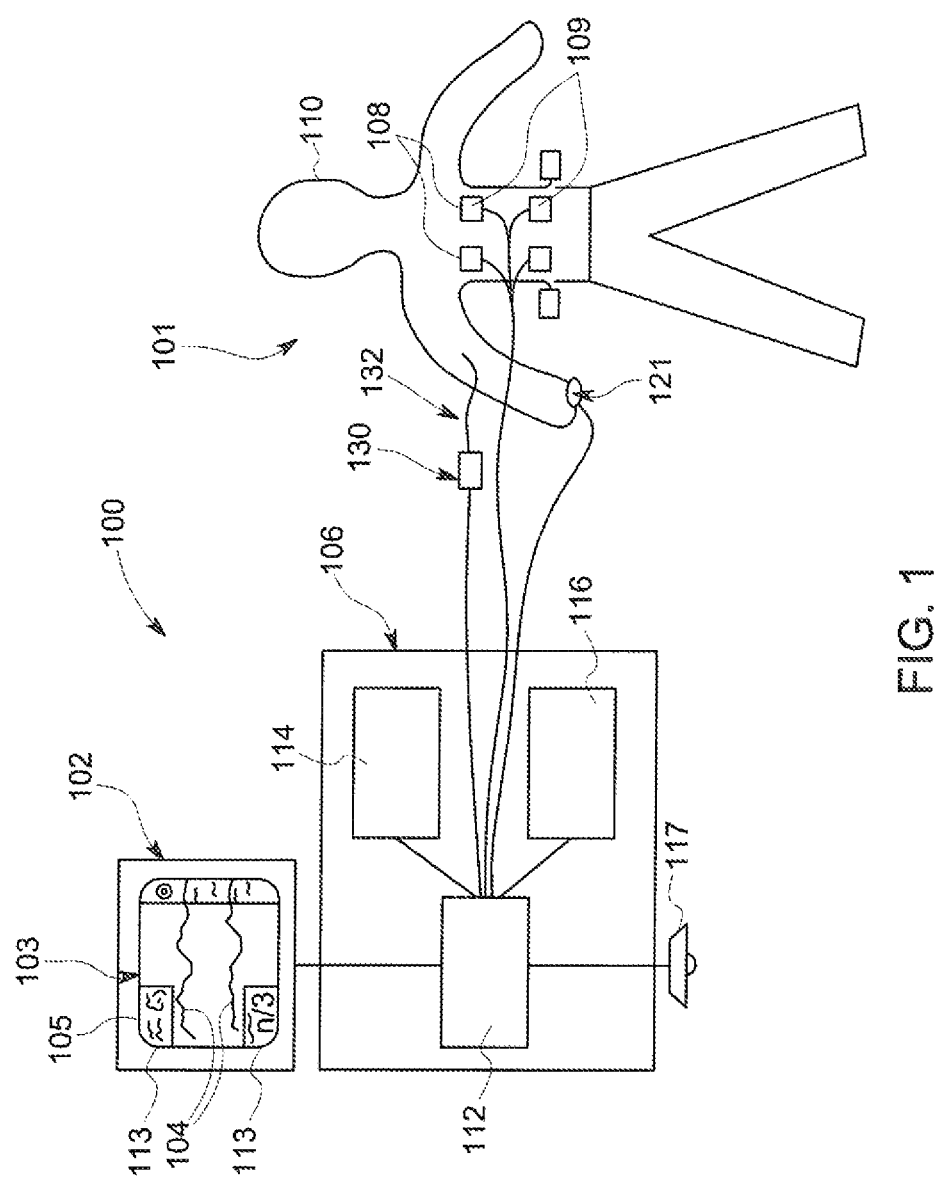
FIG. 1 is a schematic view of a monitoring device in accordance with an exemplary embodiment of the invention.

FIG. 1 illustrates an exemplary embodiment of the invention which includes a monitoring or diagnostic device 100, which can be any suitable type of monitoring device for monitoring various operating parameters of an item 101, such as a patient 110, operably connected to the device 100. The device 100 includes a display 102 of any suitable type, such as a touch screen display, having a screen 103 thereon on which the monitoring data signals 104 regarding the object 101 connected to the device 100 can be displayed. When formed as a touch screen, the display 102 can additionally function as a user interface 105 for use in controlling the operation of the device 100, though the interface 105 can be formed as a separate component connected to the device 100, if desired.

In the exemplary embodiment of FIG. 1, the device 100 takes the form of a medical monitoring device 106 that has one or more leads or sensors 108, such as ECG electrodes 109, operably connected in any suitable manner between the medical monitoring device 106 and a patient 110 in order to monitor various vital statistics of the patient 110. In addition to the electrodes 109, the device 100 can employ additional sensors 108 used to monitor other parameters or statistics of the patient 110, such as a pulse oximeter sensor 121 and/or an invasive pressure catheter 130 and invasive pressure transducer 132 to measure the blood flow and pressure of the patient 110 for comparison with the data obtained from the ECG electrodes 109.

The medical monitoring device 106 includes a central processing unit (CPU) 112 operably connected to the sensors 108 in order to receive and process data from the sensors 108 on the various vital statistics or parameters of specified bodily functions of the patient 110, which can relate to cardiac functions, or any other bodily functions or systems which are also contemplated as being within the scope of the present invention. These parameters can then be transmitted from the CPU 112 to the display 102 for presentation in various display areas 113 (FIG. 2) on the screen 103 of the display 102 for review by an individual monitoring the patient 110 via the display 102.

The device 100 also includes memory module 114, which can take the form of any suitable computer-readable storage media, for example a RAM module, and an electronic storage medium, component or database 116, each of which are operably connected to the CPU 112 in order to assist in the monitoring function of the device 100 using the data signals 104 supplied to the CPU 112 via the sensors 108. The device 100 also includes an audio speaker 117 for enabling the device 100 to provide audible indications of various operating characteristics of the device 100.

Electronic storage medium 116 includes certain information regarding the predetermined normal or acceptable values and/or ranges for the operating parameters, vital statistics or physiological parameters for the patient 110 relating to those parameters sensed by the sensors 108 connected to the device 100. These stored value and/or ranges function as criteria for comparison by the CPU 112 with the incoming data signals 104 from the sensors 108 and to determine whether the current vital statistics or physiological parameters of the patient 110 indicate an alarm condition with regard to the patient 110. The stored values and/or ranges for the incoming data signals 104 on the different physiological parameters and vital statistics received by the CPU 112 from the various sensors 108 can include minimum and maximum values of the sensed parameters, minimum and maximum value or frequency ranges for the sensed physiological parameters, the amount of time a particular parameter remains above a defined value, or any other suitable aspect of the incoming data signals 104 to be used in the determination of an alarm event or condition, such as an arrhythmia. The ranges may also include intermediate values between the minimum and maximum values to assist in determining various intermediate levels of any alarm criteria.

To determine the presence of an alarm condition, the incoming data signals 104 are compared with the relevant stored criteria by the CPU 112. If the signals 104 from the sensors 108 meet any of the stored criteria, the CPU 112 determines that an alarm condition or event, such as a cardiac alarm condition or event, is occurring/has occurred, and can operate the display 102 in manner to be described to alert the individual/person monitoring the display 102 of the alarm condition or event, and to provide the individual/person with additional information relating to the incoming data signals 104 and the related alarm condition or event.

Figure 2:
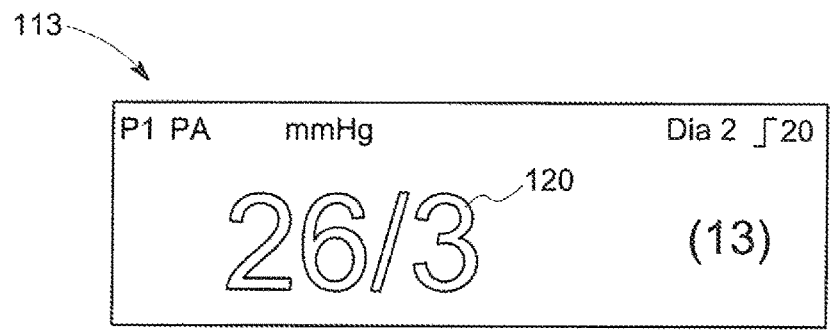
FIG. 2 is a schematic view of a monitoring device display showing no alarm event in accordance with an exemplary embodiment of the invention.
Figure 3:
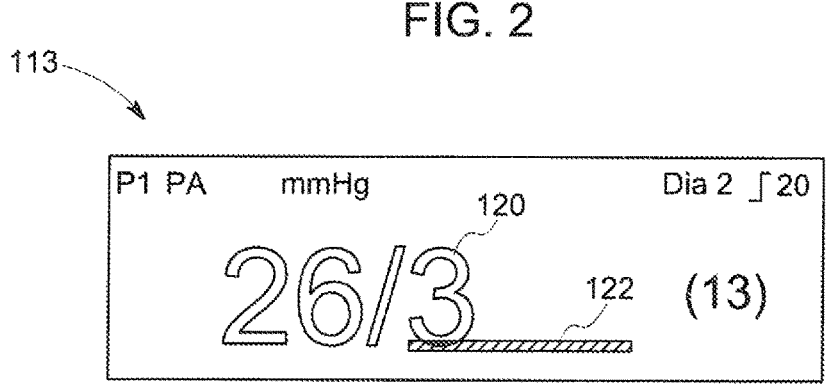
FIG. 3 is a schematic view of a monitoring device display showing a first level low or medium alarm event in accordance with an exemplary embodiment of the invention.
Figure 4:
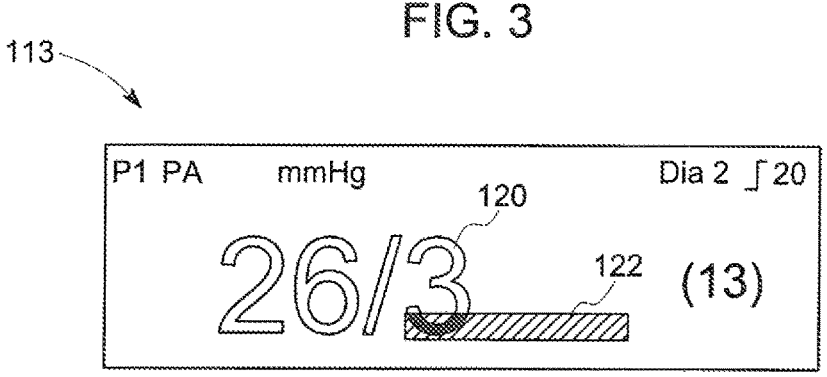
FIG. 4 is a schematic view of a monitoring device display showing a second level low or medium alarm event in accordance with an exemplary embodiment of the invention.
Figure 5:
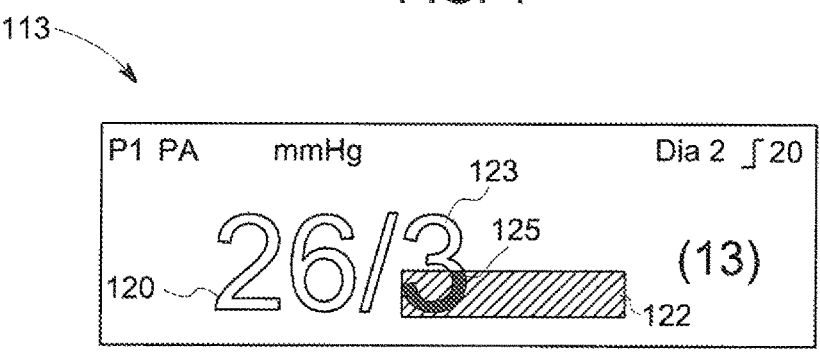
FIG. 5 is a schematic view of a monitoring device display showing a third level low or medium alarm event in accordance with an exemplary embodiment of the invention.
Figure 6:
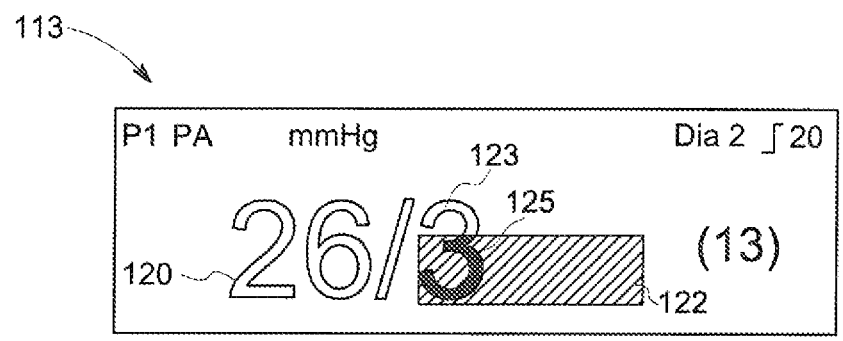
FIG. 6 is a schematic view of a monitoring device display showing a fourth level low or medium alarm event in accordance with an exemplary embodiment of the invention.
Figure 7:
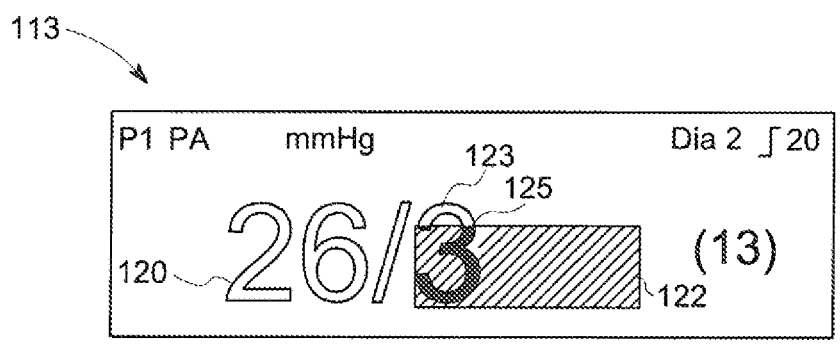
FIG. 7 is a schematic view of a monitoring device display showing a fifth level low or medium alarm event in accordance with an exemplary embodiment of the invention.

Referring now to FIGS. 2-16, the display area 113 on the screen 102 is illustrated. In the area 113, a number of parameters 120 illustrating the data provided by the signals 104 are graphically presented. As shown in FIG. 2, if none of the criteria for an alarm condition are met by the incoming data signals 104, the display area 113 illustrates the parameters 120 from the incoming data signals 104 in a normal manner. However, when an initial criteria for an alarm condition/event is met by the incoming data signals 104, as shown in FIG. 3 the CPU 112 alters the operation of the display area 113 relating to the particular parameter 120. While the alteration of the display area 113 can be performed in a number of different manners, in the exemplary embodiment shown in FIG. 3, the CPU 112 can alter the display area 113 by highlighting an alarm portion 122 of the display area 113 in which the parameter 120 is displayed on the screen 103, along with a consequent alteration of the display area 113 to ensure part of the parameter 120 displayed in the alarm portion 122 remains visible. The highlighted alarm portion 122 remains highlighted during the continued operation of the display 102 in order to draw the attention of an observing clinician to the representation of the developing alarm condition represented by the portion 122.

As new incoming data signals 104 are received by the CPU 112 and compared to the stored criteria, the CPU 112 can continually alter the operation of the display area 113 in a manner that identifies whether an alarm condition has been identified, and the severity of any existing alarm condition. In particular, as shown in FIGS. 2-7, as additional criteria for an alai in condition are met, the CPU 112 causes additional alarm portions 122 of the display area 113 to be highlighted, and additional parts of the parameter 120 displayed in the portions 122 to be consequently altered for continuous visibility, further identifying the alarm condition and its severity to the observing clinician. In the exemplary embodiment shown in FIGS. 2-7, the parameter 120 and the portions 122 are inversely colored, such that the un-highlighted portions 122 and the section 123 of the parameter 120 outside of the highlighted portions 122 appear as negatives of the highlighted portions 122 and the section 125 of the parameter 120 within the highlighted portions 122. Conversely, if the incoming data signals 104 were to indicate an improvement of the alarm condition via a reduction in the alarm criteria being met, the CPU 112 would consequently reduce the number of highlighted portions 122 of the display area 113.

Figure 8:
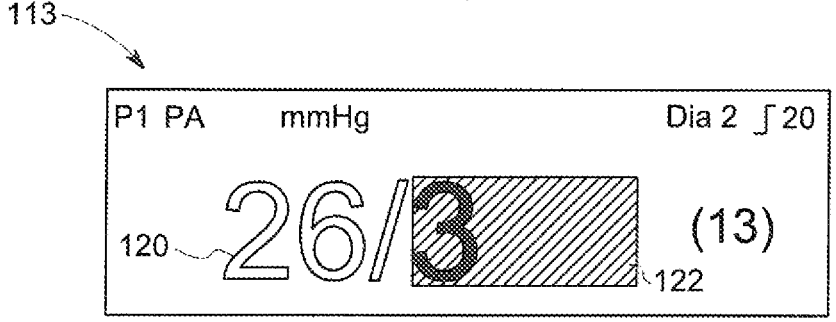
FIG. 8 is a schematic view of a monitoring device display showing a full low or medium alarm event in accordance with an exemplary embodiment of the invention.

The number of alarm portions 122 of the display area 113 that can be highlighted can be varied as desired and may be in part defined by the particular alarm condition being monitored. Also, when a set number and/or type of criteria have been met to have each portion 122 of the display area 113 highlighted, as shown in FIG. 8, a fully developed alarm condition is indicated. Additionally, in order to draw added attention to the fully developed alarm condition, the CPU 112 can operate the display area 113 to intermittently flash the highlighted portions 122 within the display area 113, which in the exemplary embodiment is achieved by continually alternating or reversing the colors used to display the parameter 120 and the highlighted portions 122, such as between the displays illustrated in FIGS. 2 and 8.

While one exemplary embodiment of the system and method of this invention can include a single progression through the operation of the alarm portions 122 of the display area 113 to indicate the development of an alarm condition, in another exemplary embodiment as shown in FIGS. 2-16, the initial highlighting of the portions 122 in FIGS. 2-8 can be utilized to indicate the development of a low or medium level alarm condition(s) or event(s) relating to the criteria met by the incoming data signals 104.

Figure 9:
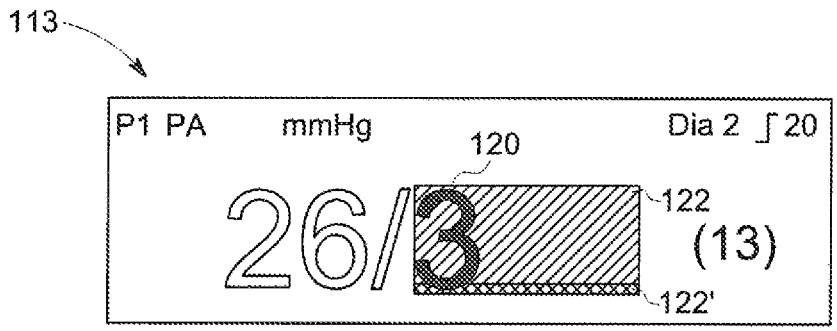
FIG. 9 is a first schematic view of a monitoring device display showing a first level medium or high alarm event in accordance with an exemplary embodiment of the invention.
Figure 10:
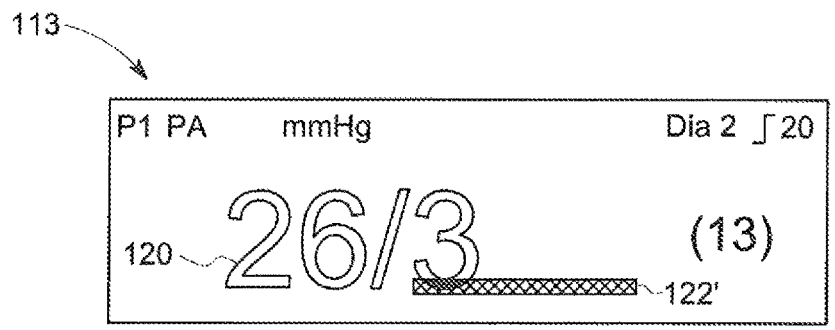
FIG. 10 is a second schematic view of a monitoring device display showing a first level medium or high alarm event in accordance with an exemplary embodiment of the invention.
Figure 11:
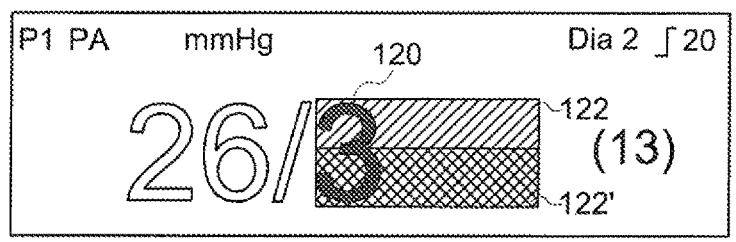
FIG. 11 is a first schematic view of a monitoring device display showing a second level medium or high alarm event in accordance with an exemplary embodiment of the invention.
Figure 12:
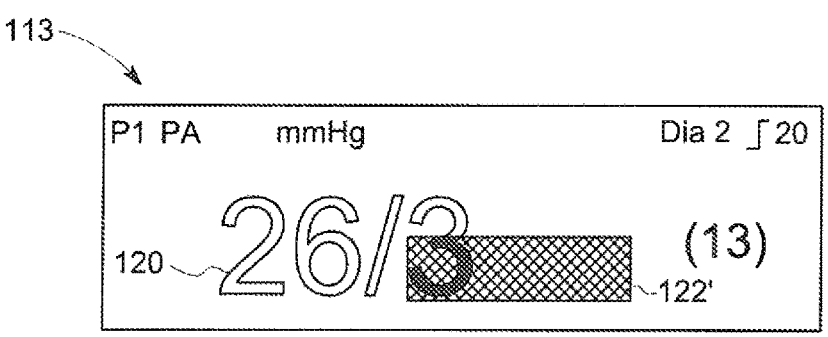
FIG. 12 is a second schematic view of a monitoring device display showing a second level medium or high alarm event in accordance with an exemplary embodiment of the invention.
Figure 13:
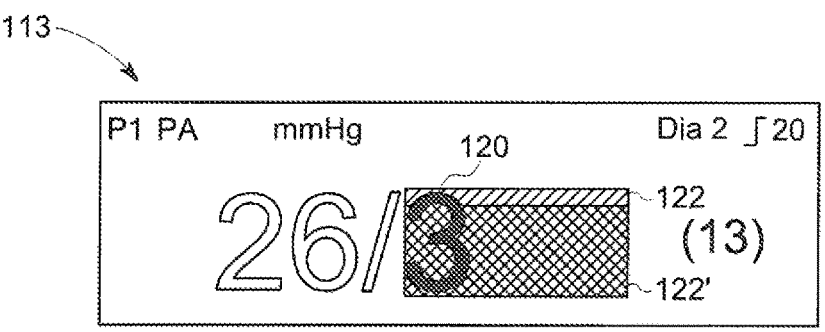
FIG. 13 is a first schematic view of a monitoring device display showing a third level medium or high alarm event in accordance with an exemplary embodiment of the invention.
Figure 14:
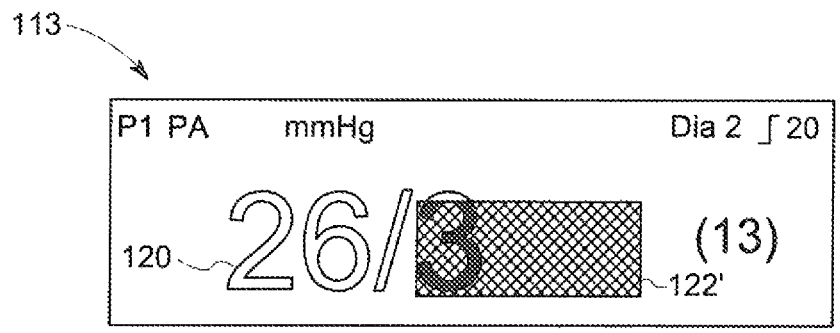
FIG. 14 is a second schematic view of a monitoring device display showing a third level medium or high alarm event in accordance with an exemplary embodiment of the invention.

However, in addition to this low or medium level alarm condition, criteria for a medium or high level alarm condition are retained in the electronic storage medium 116 for comparison with the incoming data signals 104. When one or more of the criteria for the medium or high level alarm condition is met as determined by the CPU 112, the CPU 112 operates the display area 113 to highlight an alarm portion 122' of the area 113 in a color different that than used to highlight the alarm portion 122 when a low or medium level alarm event criteria is met. In this exemplary embodiment, while the remainder of the alarm portions 122 of the display area 113 that have been highlighted as a result of the full low or medium alarm condition criteria being met remains flashing, as shown in FIGS. 9 and 10, the portion 122' indicating the medium or high alarm level criteria that has been met is highlighted in a different color from portion 122. In addition, the alarm portion 122' overlaps one or more alarm portions 122 and remains constantly highlighted, such that the portion 122' does not flash intermittently along with the remainder of the visible portions 122. Further, depending upon the desired number of levels that are defined for each of the low or medium and medium or high level alarm conditions, the size of the highlighted alarm portions 122, 122' can vary. In the exemplary embodiment of FIGS. 2-16, the low or medium alarm condition includes six (6) alarm portions 122, while the medium or high alarm condition includes only four (4) alarm portions 122'.

Looking now at FIGS. 11-14, as the incoming data signals 104 indicate more criteria for the medium or high level alarm event or condition have been met, additional portions 122' of the display area 113 are highlighted in the color different that that used for the portions 122 and overlap additional flashing portions 122. Also, the additional highlighted portions 122' are constantly highlighted or de-highlighted depending on the medium or high level criteria that are met, while the remainder of the display area 113 illustrating the remaining visible portions 122 continues to flash intermittently.

Figure 15:
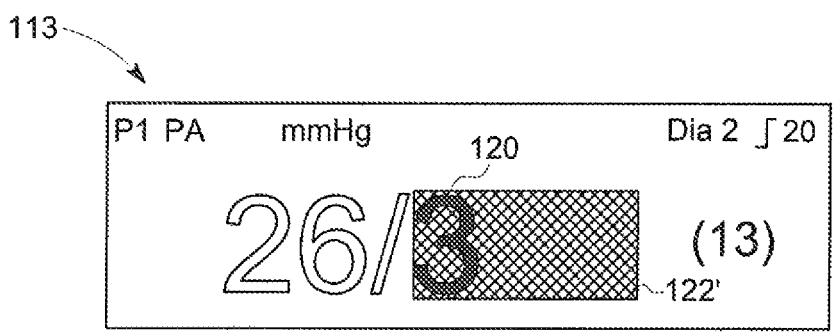
FIG. 15 is a first schematic view of a monitoring device display showing a full level medium or high alarm event in accordance with an exemplary embodiment of the invention.
Figure 16:
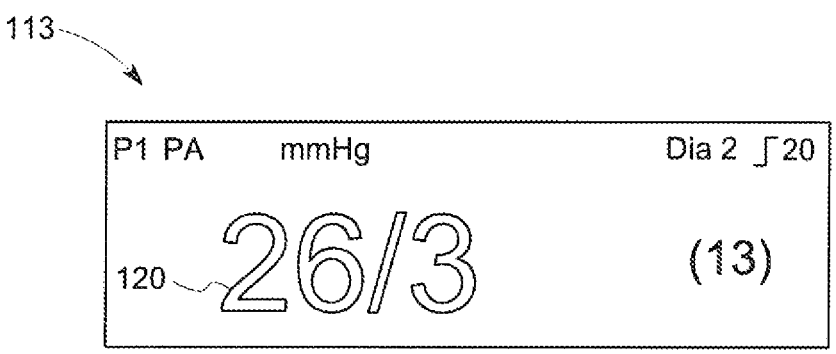
FIG. 16 is a second schematic view of a monitoring device display showing a full level medium or high alarm event in accordance with an exemplary embodiment of the invention.

Looking now at FIGS. 15-16, when a full medium or high alarm event is indicated as a result of the comparison of the incoming data signals 104 to the criteria stored in the electronic storage medium 116, the CPU 112 operates the display area 113 to flash the portions 122' intermittently, which now cover the entire area 113. This alarm indication in the display area 113 can additionally be accompanied by any other standard function of the device 106, such as an audio alarm, among others.

Thus, with this device 106 and the operation of the display area 113 in this manner corresponding to the number and level of stored criteria being met by the incoming signals 104 received by the device 106, the device 106 can indicate to the observing clinician the development and/or trend of an alarm condition in a patient 110 while using only an existing display area(s) 113 on the display screen 103 for the device 106 that already illustrates the parameters 120 directly related to the alarm condition being determined. In this manner of one exemplary illustrated embodiment, the portions 122,122' relating to the display of the alarm condition are contained entirely within an existing display area 113 of the screen 103 to eliminate the need for additional display areas to be added to the screen 103 to separately illustrate the alarm trends and/or conditions. Further, and the observing clinician is visually provided with and/or directed to the information related to the developing alarm condition in a clear and easily visible manner in order to be able to alleviate and/or prevent the condition from worsening.

In other exemplary embodiments of the present invention, more than one display area 113 can be operated on the screen 103 to highlight sections 122 of the area 113 to illustrate a developing alarm condition relevant to the parameter 120 being displayed in the particular display area 113. Further, the various portions 122 being highlighted can be accompanied by other indications from the device 106, such as audible indications from an associated speaker 117. Also, additional levels of alarm events can be included in the highlighting provided by the display 102, such that, for example, the display 102 can be configured to individually represent escalations and de-escalations of a low alarm event, a medium alarm event and a high alarm event, or any number of separate alarm events.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A monitoring device for providing information on data obtained from sensors operably connected to the device, the device comprising:
    a) a central processing unit configured to receive incoming data signals from a sensor concerning a current physiological parameter and to compare the incoming data signals to predetermined alarm criteria for the current physiological parameter to determine an alarm condition; and
    b) a display operably connected to the central processing unit, the display including a display screen including a display area configured to visually represent the incoming data signals concerning the current physiological parameter relating to a determined alarm condition on an alarm portion of the display area in a visually distinct manner from a remainder of the display area,
    wherein the alarm portion is contained entirely within the display area to overlay a representation of the current physiological parameter within the display area,
    wherein the device is configured to visually represent a value for the current physiological parameter in the display area in a visually distinct manner from the alarm portion of the display area,
    wherein the value of the current physiological parameter and the alarm portion of the display area are inversely colored, and
    wherein the device is configured to intermittently switch the colors of the value of the current physiological parameter and the alarm portion of the display area.

2. A monitoring device for providing information on data obtained from sensors operably connected to the device, the device comprising:
    a) a central processing unit configured to receive incoming data signals from a sensor concerning a current physiological parameter and to compare the incoming data signals to predetermined alarm criteria for the current physiological parameter to determine an alarm condition; and
    b) a display operably connected to the central processing unit, the display including a display screen including a display area configured to visually represent the incoming data signals concerning the current physiological parameter relating to a determined alarm condition on an alarm portion of the display area in a visually distinct manner from a remainder of the display area,
    wherein the alarm portion is contained entirely within the display area to overlay a representation of the current physiological parameter within the display area,
    wherein the alarm portion is a first alarm portion,
    wherein the device is configured to visually represent the incoming data signals concerning the current physiological parameter relating to a second determined alarm condition on a second alarm portion of the display area in a visually distinct manner from the first alarm portion and the remainder of the display area,
    wherein the device is configured to represent the first alarm portion in a first color, the second alarm portion in a second color and the remainder of the display area in a third color, and
    wherein the device is configured to intermittently switch the colors of the first alarm portion and the remainder of the display area while maintaining the color of the second alarm portion constant.

3. The device of claim 2 wherein the first alarm portion and the second alarm portion overlap.

4. A monitoring device for providing information on data obtained from sensors operably connected to the device, the device comprising:
    a) a central processing unit configured to receive incoming data signals from a sensor concerning a current physiological parameter and to compare the incoming data signals to predetermined alarm criteria for the current physiological parameter to determine an alarm condition; and
    b) a display operably connected to the central processing unit, the display including a display screen including a display area configured to visually represent the incoming data signals concerning the current physiological parameter relating to the determined alarm condition on an alarm portion of the display area in a visually distinct manner from a remainder of the display area,
    wherein the alarm portion overlays a portion of a representation of the current physiological parameter within the display area, and a size of the overlaid portion reflects a severity of the alarm condition determined for the current physiological parameter.

5. The device of claim 4 wherein the device is configured to visually represent the alarm portion of the display area in a first color and representing the remainder of the display area in a second color.

6. The device of claim 4 wherein the device is configured to visually represent a value for the current physiological parameter in the display area in a visually distinct manner from the alarm portion of the display area.

7. The device of claim 6 wherein the value of the current physiological parameter and the alarm portion of the display area are inversely colored.

8. The device of claim 4 wherein the alarm portion is a first alarm portion, and wherein the device is configured to visually represent the incoming data signals concerning the current physiological parameter relating to a second determined alarm condition on a second alarm portion of the display area in a visually distinct manner from the first alarm portion and the remainder of the display area.

9. The device of claim 8 wherein the device is configured to represent the first alarm portion in a first color, the second alarm portion in a second color and the remainder of the display area in a third color.

10. The device of claim 4 wherein the alarm portion covers the entire display area to indicate a fully developed alarm condition.

11. A method for visually indicating the presence and severity of an alarm condition determined from incoming data signals on a display screen, the method comprising the steps of:
   a) receiving incoming data signals from a sensor concerning a current physiological parameter;
   b) displaying a value of the current physiological parameter at a display area on a display screen;
   c) comparing the incoming data signals from the sensors with predetermined criteria for determining an alarm condition; and
   d) overlaying a highlighted alarm portion in a visually distinct manner directly on a portion of the display of the value for the current physiological parameter in the display area, wherein a size of the overlaid portion reflects a severity of the alarm condition determined for the current physiological parameter.

12. The method of claim 11 wherein the highlighted alarm portion covers the entire display area to indicate a fully developed alarm condition.

13. A method for visually indicating the presence and severity of an alarm condition determined from incoming data signals on a display screen, the method comprising the steps of:
   a) providing a monitoring device including a central processing unit configured to receive incoming data signals from a sensor concerning a current physiological parameter, and to compare the incoming data signals to predetermined criteria for determining an alarm condition, and a display operably connected to the central processing unit and including the display screen and a display area on the display screen in which a value of the current physiological parameter is represented;
   b) comparing the incoming data signals from the sensors with the criteria for the alarm condition; and
   c) highlighting an alarm portion of the display area in a visually distinct manner from a remainder of the display area,
   d) re-comparing the incoming data signals from the sensors with the criteria for the alarm condition after representing the alarm portion on the display area; and
   e) highlighting the alarm portion of the display area represented in a visually distinct manner from a remainder of the display area corresponding to any increase or decrease in the severity of the alarm condition determined from the comparison of the incoming data signals from the sensors with the criteria for the alarm condition,
   wherein the step of highlighting the alarm portion of the display area in a visually distinct manner from a remainder of the display area further comprises overlaying the alarm portion in a visually distinct manner directly on the display of the value for the current physiological parameter in the display area, and
   wherein the step of highlighting the alarm portion of the display area in a visually distinct manner comprises highlighting the alarm portion in a color different from the remainder of the display area.

14. The method of claim 13 wherein the criteria for the alarm condition include criteria for a first alarm condition and criteria for a second alarm condition, and wherein the step of highlighting the alarm portion of the display area comprises the steps of:
   f) highlighting a number of first alarm portions in the display area corresponding to any increase or decrease in the severity of the alarm condition determined from the comparison of the incoming data signals from the sensors with the criteria for the first alarm condition; and
   g) highlighting a number of second alarm portions in the display area corresponding to any increase or decrease in the severity of the alarm condition determined from the comparison of the incoming data signals from the sensors with the criteria for the second alarm condition.

15. The method of claim 14 wherein the highlighting of the number of first alarm portions and the highlighting of the number of second alarm portions are each visually distinct from a display of the current physiological parameter in the display area.

16. The method of claim 14 wherein the second alarm portions overlap the first alarm portions.

17. The method of claim 14 wherein the number of first alarm portions is different than the number of second alarm portions.

18. The method of claim 13 wherein the step of highlighting the alarm portion comprises increasing or decreasing the size of the alarm portion corresponding to the increase or decrease in the severity of the alarm condition determined from the comparison of the incoming data signals from the sensors with the criteria for the alarm condition.

* * * * *